(12) United States Patent
Larsen et al.

(10) Patent No.: US 8,907,251 B2
(45) Date of Patent: *Dec. 9, 2014

(54) PERSONAL THERMAL REGULATING DEVICE

(71) Applicant: 3Eye, LLC, Portland, OR (US)

(72) Inventors: Walter G. Larsen, Portland, OR (US); Michael J. Adler, Portland, OR (US)

(73) Assignee: 3Eye, LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/169,110

(22) Filed: Jan. 30, 2014

(65) Prior Publication Data

US 2014/0200637 A1 Jul. 17, 2014

Related U.S. Application Data

(63) Continuation of application No. 13/742,258, filed on Jan. 15, 2013, now Pat. No. 8,658,943.

(51) Int. Cl.
*A61F 7/00* (2006.01)
*H05B 3/02* (2006.01)
*H05B 3/06* (2006.01)
*A61F 7/02* (2006.01)

(52) U.S. Cl.
CPC . *A61F 7/02* (2013.01); *A61F 7/007* (2013.01); A61F 2007/0096 (2013.01); A61F 2007/0296 (2013.01); A61F 2007/008 (2013.01); A61F 2007/0093 (2013.01); A61F 2007/0086 (2013.01); A61F 2007/0226 (2013.01); A61F 2007/0084 (2013.01); A61F 2007/0007 (2013.01); A61F 2007/0078 (2013.01); *H05B 3/06* (2013.01); A61F 2007/0095 (2013.01); A61F 2007/0246 (2013.01); A61F 2007/0233 (2013.01)

USPC .................... 219/211; 607/108; 607/109

(58) Field of Classification Search
CPC ............ A61F 2007/0007; A61F 7/02; A61F 2007/0071; A61F 2007/0073–2007/0075; A61F 2007/0078; A61F 2007/008; A61F 2007/0093; A61F 2007/0095; A61F 2007/0096; A61F 2007/0228; A61F 2007/0231; H05B 1/0252; H05B 2203/017

See application file for complete search history.

(56) References Cited

U.S. PATENT DOCUMENTS

| | | | | |
|---|---|---|---|---|
| 2,038,275 A * | 4/1936 | Fogg | | 219/527 |
| 2,429,583 A * | 10/1947 | Ogle | | 607/109 |
| 2,919,735 A * | 1/1960 | Prietzsch | | 607/112 |
| 5,609,619 A * | 3/1997 | Pompei | | 607/104 |
| 5,802,865 A * | 9/1998 | Strauss | | 62/259.3 |
| 5,970,718 A * | 10/1999 | Arnold | | 62/3.5 |
| 6,125,636 A * | 10/2000 | Taylor et al. | | 62/3.5 |
| 6,165,208 A * | 12/2000 | Reyes et al. | | 607/112 |
| 6,189,327 B1 * | 2/2001 | Strauss et al. | | 62/259.3 |
| 6,438,964 B1 * | 8/2002 | Giblin | | 62/3.5 |

(Continued)

*Primary Examiner* — Joseph M Pelham
(74) *Attorney, Agent, or Firm* — Patrick D. Boyd; Paul B. Heynsenns; Ater Wynne LLP

(57) ABSTRACT

A personal thermal regulating device (PTRD) typically includes a heat generating device, a power source, a switchable control operably coupled with each of the heat generating device and the power source, and a head retention device coupled with the heat generating device and configured to retain the heat generating device positioned centrally at and in thermally conductive contact with a user's forehead. The present invention affects a tangible warming of the extremities, particularly the hands and feet, extending retention of manual dexterity and peripheral comfort under cold conditions.

29 Claims, 10 Drawing Sheets

(56) References Cited

U.S. PATENT DOCUMENTS

| | | | |
|---|---|---|---|
| 6,554,787 B1* | 4/2003 | Griffin et al. | 602/74 |
| 6,948,322 B1* | 9/2005 | Giblin | 62/3.5 |
| 8,087,254 B2* | 1/2012 | Arnold | 62/3.5 |
| 8,236,038 B2* | 8/2012 | Nofzinger | 607/109 |
| 2001/0039442 A1* | 11/2001 | Gorge et al. | 607/109 |
| 2001/0051820 A1* | 12/2001 | Rich | 607/109 |
| 2004/0059400 A1* | 3/2004 | Lin | 607/109 |
| 2005/0222654 A1* | 10/2005 | Brown | 607/109 |
| 2007/0225783 A1* | 9/2007 | Koby et al. | 607/108 |
| 2008/0004679 A1* | 1/2008 | Naghavi et al. | 607/108 |
| 2010/0037366 A1* | 2/2010 | Panicali | 2/171.2 |
| 2010/0198322 A1* | 8/2010 | Joseph et al. | 607/108 |
| 2011/0066217 A1* | 3/2011 | Diller et al. | 607/108 |
| 2012/0143079 A1* | 6/2012 | Lia et al. | 600/549 |

* cited by examiner

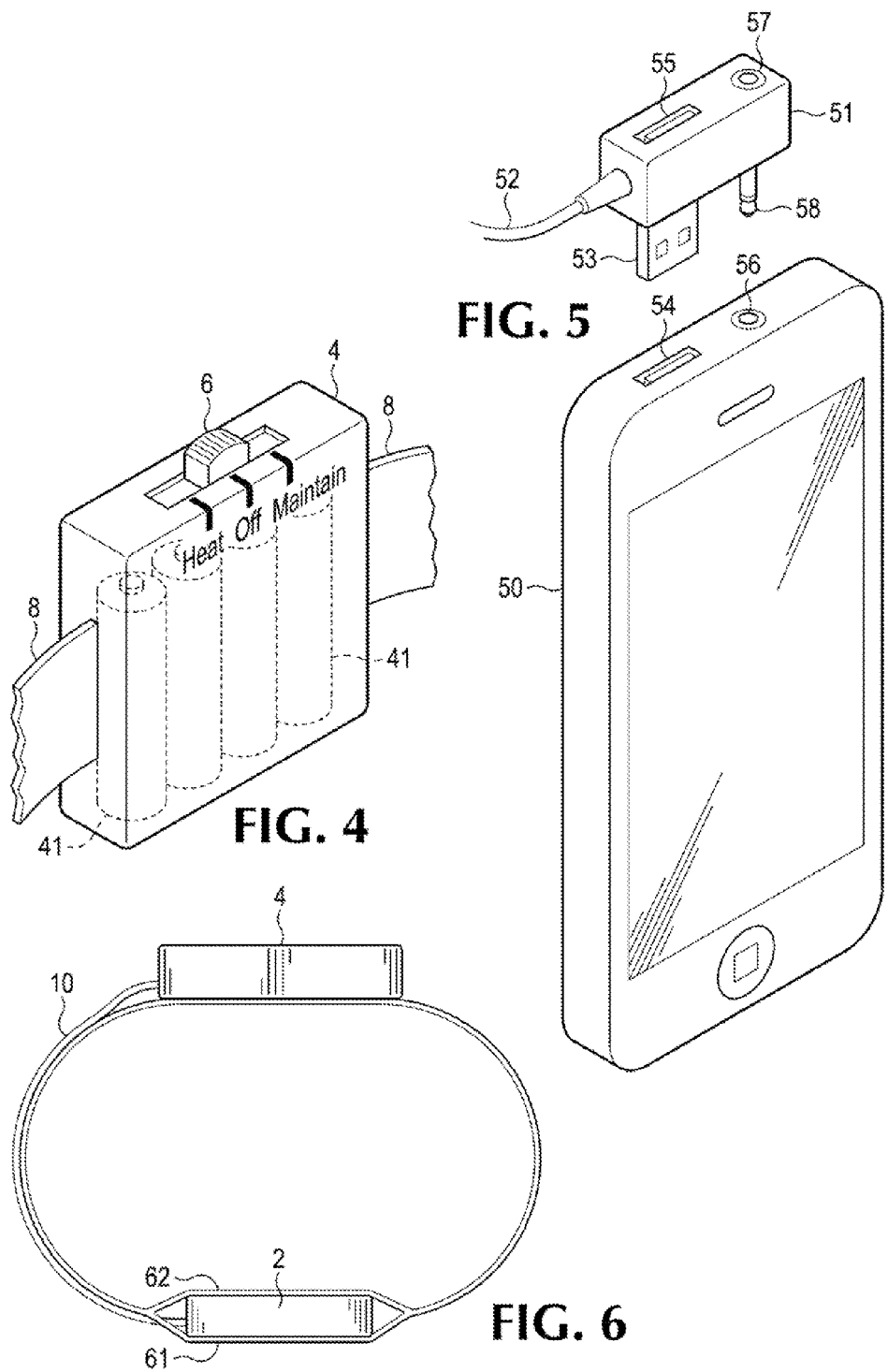

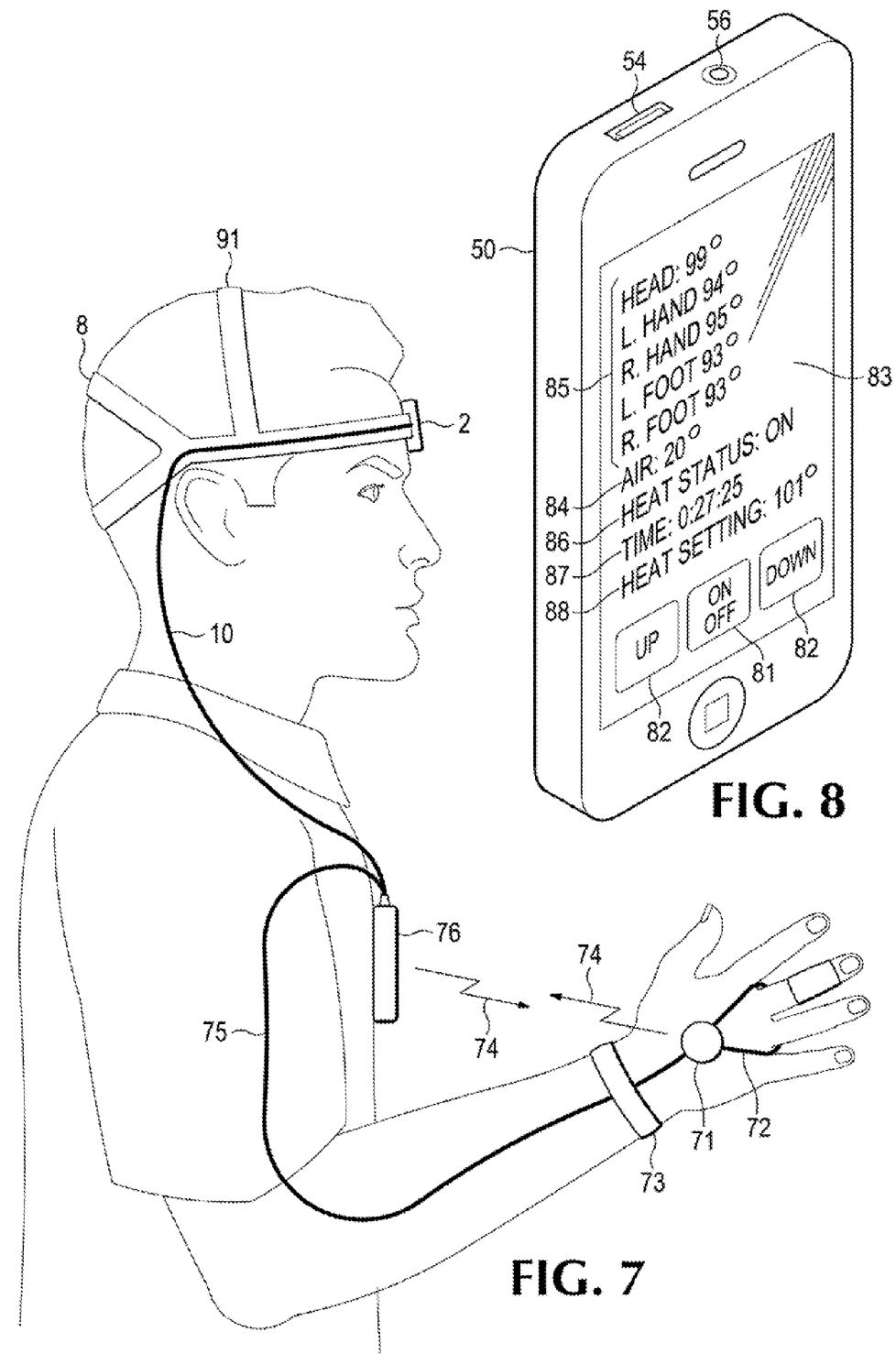

PERSONAL THERMAL REGULATING DEVICE

RELATED APPLICATIONS

This application is a continuation of, and claims the benefit of priority to, co-pending application Ser. No. 13/742,258, entitled PERSONAL THERMAL REGULATING DEVICE and filed Jan. 15, 2013, the entire disclosure and contents of which is incorporated into this application by this reference.

FIELD OF THE INVENTION

The invention relates generally to the field of personal thermal regulating devices, and more particularly relates to a device, system and method for remotely inducing warming of the peripheral anatomy of a user.

BACKGROUND OF THE INVENTION

It is well-established that humans lose a great amount of body heat through their heads when exposed to a cold environment. Likewise, the anatomical extremities—feet and toes, hands and fingers, noses, ears, etc.—lose heat more quickly than the body core, and are subject to frostbite and other dangerous conditions in cold environments if not protected. Additionally, when extremities such as fingers and toes become cold, numbness develops, motor functions and dexterity decline, and pain is amplified in response to even minor impacts. Therefore, cooling of the anatomical extremities substantially degrades human performance, comfort and safety.

Therefore, hats, hoods, balaclava, and other head coverings are employed in such conditions to provide an insulating layer, reducing the rate of heat loss through the head. Likewise, gloves, mittens, pockets, and other protective coverings are employed to prevent or delay heat loss through the extremities. However, protective, insulating coverings cannot maintain thermal stasis over time; they merely slow the rate of heat loss. Therefore, their benefit and effectiveness decreases over the course of extended exposure to ambient cold.

Furthermore, the effectiveness of hand coverings is frequently closely related to their thickness, which consequently negatively affects manual dexterity, as anyone attempting to remove car keys from their pocket while wearing gloves will readily recognize. When faced with the need to perform a manual task requiring dexterity while exposed in a cold environments, removing one's gloves is an intuitive and common response. However, manual dexterity is likewise reduced when the hands and fingers become cold due to such exposure. Therefore, performing dexterous tasks in cold weather remains a significant challenge, typically addressed by alternatingly exposing hands to perform tasks, then covering and warming them again to prevent discomfort and frostbite.

Perhaps man's oldest means for directly heating the extremities is the use of an open fire, perhaps followed by the placement of warmed rocks beneath blankets or into the clothing to provide a portable heating means. Indeed, protecting extremities from the cold by the use of protective coverings or the direct application of heat from an extrinsic source (e.g., fire), likely date from the dawn of man as a species.

Many devices have been developed and used over the years to provide direct and portable heating to the anatomical extremities. Such devices most typically include electrically-heated gloves, socks and boots; hand-held warmers utilizing electricity, combustible fuels, or chemical compounds reacting exothermically. However, in order to be effective, each extremity must be exposed to an associated heat source, requiring multiple devices each sized and configured sufficiently to deliver heating to a significant portion of a specific appendage. For example, shoes do not fit hands, and a left boot does not typically (comfortably) fit a right foot; therefore, each appendage requires a separate, specifically configured device to adequately deliver warming to that appendage. Further, because different types of outdoor activities frequently require differently configured types of footwear or hand coverings, the number, types, and costs of prior art extremity-warming equipment can rapidly escalate for an individual user.

While sufficient caloric consumption can help maintain body warmth via metabolic warming, the benefits of this heat source are likewise limited. Metabolic processes warm the body core to some extent, but the extremities benefit to a notably lesser extent due in part to the reduced rate and volume of blood flow as compared to the body core and the head. In particular, Caloric consumption diverts blood flow to the gastrointestinal tract for digestion, shunting blood from the periphery. Further, blood vessels in the extremities ordinarily constrict (i.e., vasoconstriction) when exposed to cold conditions in a natural response designed to help preserve the core body temperature.

Several related but distinct concepts are known in the art. For example. U.S. Pat. No. 6,792,624 to Simmons, entitled 'Temperature Regulating Cap,' (the '624 patent) describes that a head-worn, temperature-regulating cap can include a receptacle or pocket to accommodate an air activated heating pack. However, the '624 patent's expressed purpose is to heat the head of the user, and the heating pack is described as being placed in contact with the top of the user's head. The '624 patent neither describes positioning the heating source at, nor recognizes any benefit or design to provide for thermally affecting the extremities by heating applied to, a central portion of a user's forehead. Likewise, the '624 patent does not describe or contemplate any use of sensors for thermal regulation, nor a switched control for regulating the application of heat, nor a power source for extended use without the use of extrinsic reheating sources, nor numerous other of the beneficial features of applicants' invention described herein according to several embodiments.

Another device, known commercially as the HAMMACHER SCHLEMMER HEADACHE RELIEVING WRAP, the purpose of which is to relax tense muscles and thereby provide relief from migraine and tension headaches, likewise includes an insulated, size-adjustable headband used to retain reusable gel packs in proximity to a user's head. However, as with patent '624, this device also fails to comprehend any heating effect of the extremities, and does not include or disclose numerous other of the beneficial features of applicants' inventive embodiments.

Localized application of heat or cold has long been used to provide benefits to immediately affected portions of the head—e.g., for reduction or prevention of inflammation, headache relief, fever reduction, nausea reduction, to improve wakefulness, to stem a nosebleed, for general comfort, and other such uses. Scientific evidence shows that applying cold to the forehead decreases blood flow to the hands and feet, as documented in *The Cold Pressor Test: Vascular and Myocardial Response Patterns and their Stability* by Patrice G. Saab et al. (*Psychophysiology*, 30, pp. 366-373, Cambridge University Press (1993)). Applicants are unaware, however, of any recognition in the art of the use of heat applied to the central forehead region to specifically affect a beneficial warming response in the peripheral regions, particularly in the extremities such as the arms, hands, legs and feet.

BRIEF DESCRIPTION OF THE DRAWINGS

FIG. 4 depicts in cutaway view a power source and switchable control, according to an embodiment of the invention.

FIG. 5 depicts a Connector of a PTRD coupled with a portable electronic device, according to an embodiment of the invention.

FIG. 6 depicts in a cutaway plan view a heat generating device disposed between material layers of a PTRD, according to an embodiment of the invention.

FIG. 7 depicts an embodiment of a PTRD worn by a user as during use, according to an embodiment of the invention.

FIG. 8 depicts a graphical user interface (GUI) of a switchable control displayed at a display device of a portable electronic device, according to an embodiment of the invention.

DETAILED DESCRIPTION OF THE PREFERRED EMBODIMENTS

The present invention utilizes a presently poorly understood physiological response to provide peripheral warming by applying active warming (rather than merely an insulating material) at a central portion of a user's forehead. The response has been anecdotally noted, by the listed inventors, to affect a tangible warming of the extremities, particularly the hands and feet. The warming effect is typically not instantaneous, but instead develops over a course of minutes or tens of minutes. As such, the peripheral warming reflects a reciprocal trend relative to, and offsetting to some degree, the trend of cooling at the extremities through natural radiated heat loss. Therefore, one benefit of the invention described herein is to extend the length of time one can retain manual dexterity and peripheral comfort under cold conditions. In particular, one goal of the inventive embodiments disclosed herein is to help a user attain a qualitative feeling of comfort and adequate warmth in their peripheral extremities (e.g., appendages, digits, etc.).

Figure 1A:
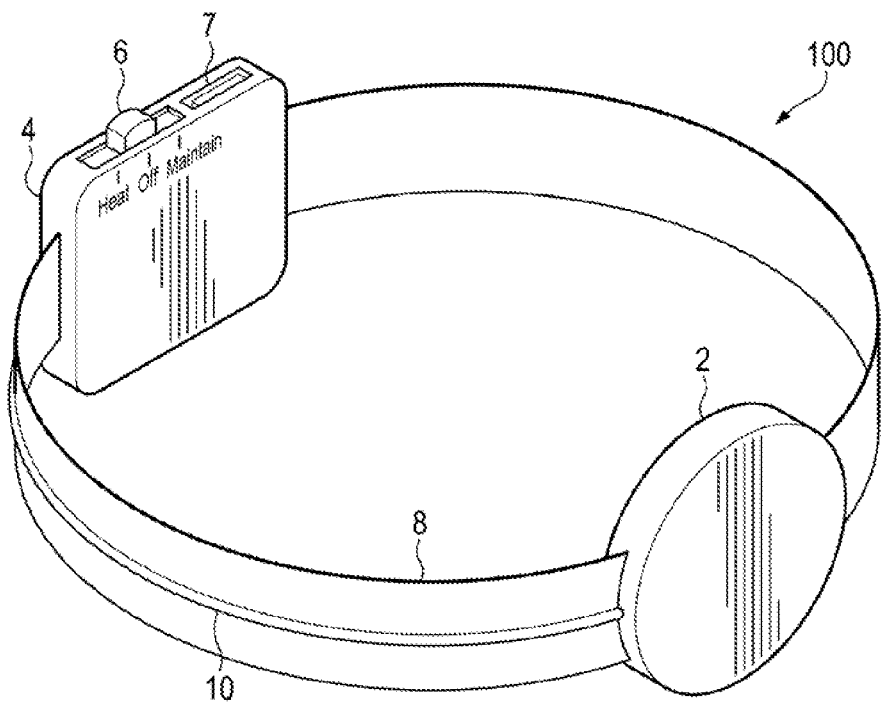
FIGS. 1a-1b depict a Personal Thermal Regulating Device (PTRD), according to alternative embodiments of the invention.
Figure 1B:
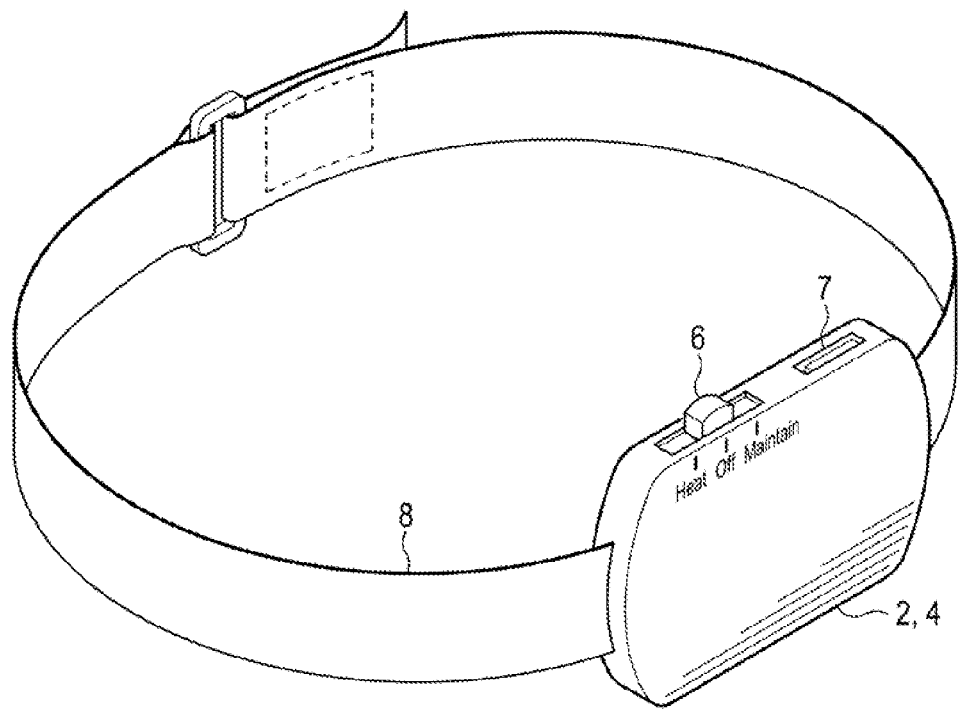

FIGS. 1a and 1b, depict embodiments of the invented device, referred to herein as a Personal Thermal Regulating Device, or 'PTRD' 100. A typical PTRD includes a heat generating device 2, a power source 4, a switchable control 6 operably coupled with each of the heat generating device and the power source, and a head retention device 8 coupled with the heat generating device.

The heat generating device 2, or 'heating element,' can be a physically separate component relative to the power source 4 or the switchable control 6, as shown in FIG. 1a, or can be included together with either or both of the power source and the switchable control, as shown in FIG. 1b. In either embodiment, these three components remain operably coupled with one another by signal conveying means 10, such as an electrically conductive lead (e.g., wires, printed circuits, etc.), or corresponding wireless signal-sending and signal-receiving devices, or other signal conducting pathways as are known in the art.

The heating element itself is most typically an electrically-powered heat generating device, for example, one utilizing electrical resistance to produce heat. One such example is the Eneloop Kairo Rechargeable Portable Electric Hand Warmer from Sanyo Electric Co. Ltd. of Japan. Alternatively, a thermoelectric cooling (TEC) device utilizing the Peltier Effect can be used, positioned so that the heat producing side of the TEC is presented toward the user's forehead and the cooling side is directed away from the user. In still other embodiments, a heating element can be a single-use pack that produces heat when exposed to air, or that produces heat by combustion of a flammable gas, or any other compact heating device that can be selectively activated by a user and can produce heat within a range of approximately one hundred five to one hundred thirty-five degrees Fahrenheit (~105-135° F.; ~40.5-57.2° C.) is believed to provide beneficial results.

Figure 2A:
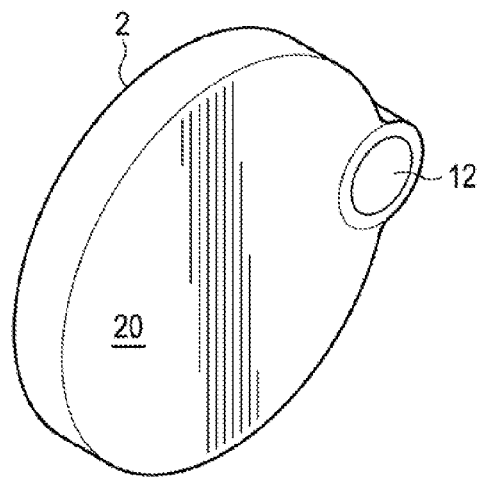
FIGS. 2a-2c depict three heat generating devices each with an integrated thermal sensor, according to alternative embodiments of the invention.
Figure 2B:
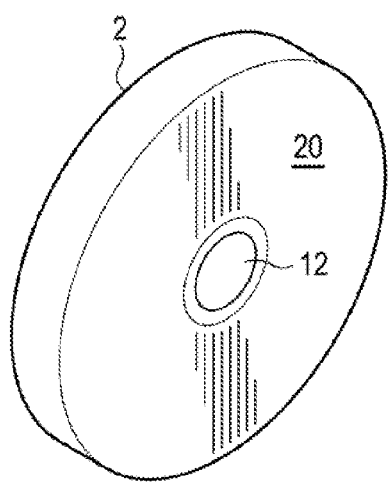
Figure 2C:
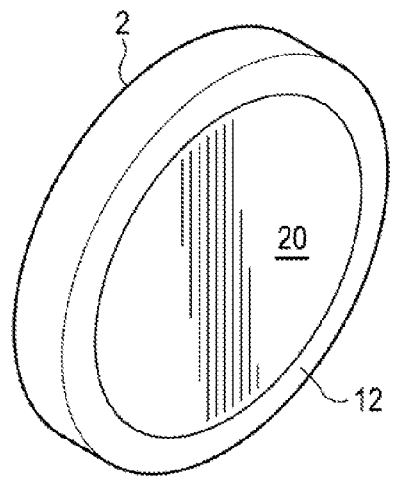
Figure 3A:
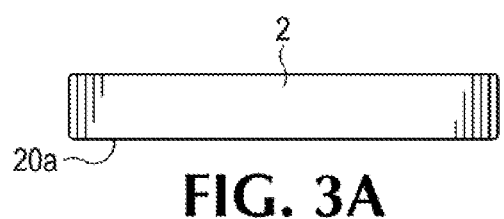
FIGS. 3a-3b depict in a plan view two heat generating devices according to alternative embodiments of the invention.
Figure 3B:
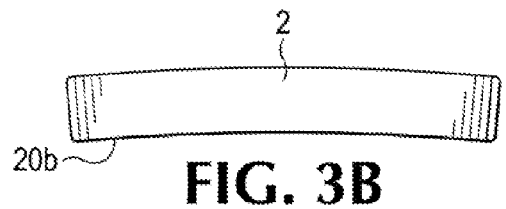
Figure 9A:
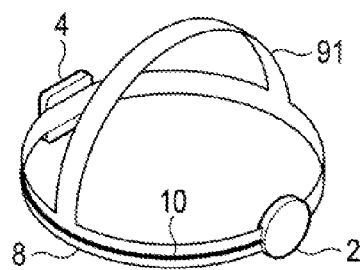
FIG. 9a-9f depict several contemplated head retention devices, according to alternative embodiments of the invention.
Figure 9B:
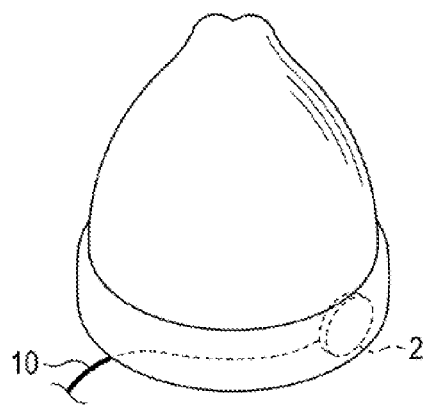
Figure 9C:
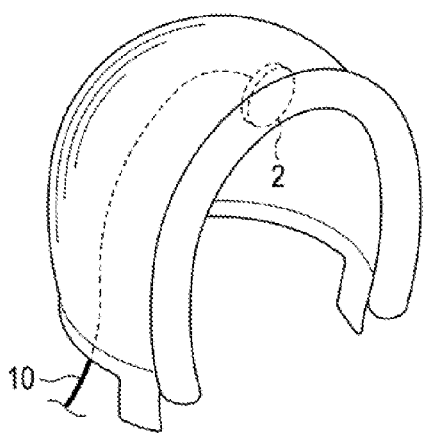
Figure 9D:
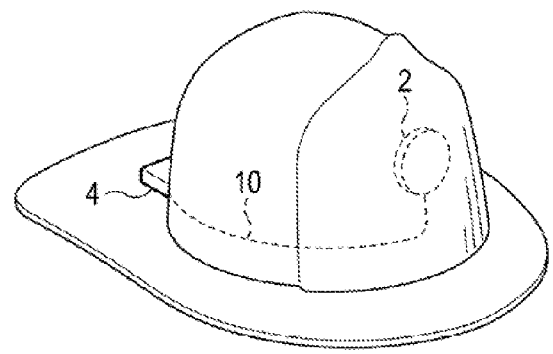
Figure 9E:
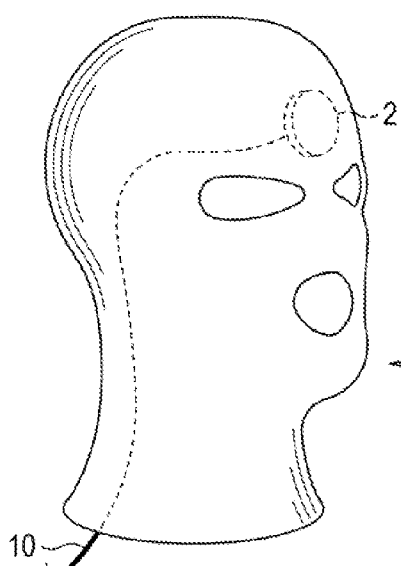
Figure 9F:
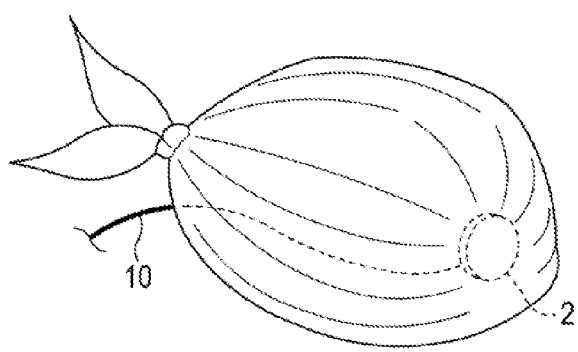

The heating element 2 is not limited to any particular exterior shape, dimension, or material, but will typically include a substantially planar user-confronting surface 20, as shown in FIGS. 2a-2c. According to alternative contemplated embodiments, applicants intend the term "substantially planar" to encompass not only embodiments of a user-confronting surface that is actually planar, as shown at 20a in FIG. 3a, but also embodiments in which the plane of the user-confronting surface is moderately curved, as shown at FIG. 3b, enabling all or most of the user-confronting surface to closely correspond to the left-to-right curvature of a user's forehead.

The heating element 2 can additionally include a thermal sensor 12 coupled therewith, and configured to detect, measure, and/or indicate either a thermal condition of the heating element or a thermal condition of a surface proximate to and confronting the heating element. The 409A reusable medical skin surface probe from Medical Specialties of Hampton, Va. is an non-exclusive example of a thermal sensor that can be used in an embodiment of the invention.

FIGS. 2a-2c depict alternative embodiments of a thermal sensor 12 integrated with the heating element 2, and in particular, the arrangement of these two features as presented at a user-confronting surface of the heating element. The thermal sensor 12 shown in FIG. 2a is disposed at an edge of the user-confronting surface 20, while the thermal sensor is surrounded by the heating element in FIG. 2b, and conversely, the thermal sensor surrounds the heating element in FIG. 2c.

The thermal sensor 12 is particularly useful for determining when the heating element has raised the thermal condition of the user's forehead to a predetermined target temperature, which determination can then be used to affect an operating condition of the PTRD. For example, the heating element 2 may operate in a warm-up or "Heat" mode until a signal from the thermal sensor indicates that either of the heating element or a portion of the user's forehead has reached a predetermined target temperature. Upon detecting such indication, the switchable control 6 can actuate a visual, audible, vibratory, or other user-detectable indicator, enabling the user to elect to either continue the same operating mode or to instead manually or otherwise alter the operating mode of the PTRD. Alternatively, the switchable control can include processor-executable coded instructions configured, when executed, to affect an operating mode of the PTRD according to a predetermined scheme upon receipt and detection of a signal from the thermal sensor.

Alternative operating modes can include a "Maintain" mode, configured to maintain a thermal condition of either or both of the heating element or a portion of the user's forehead at a predetermined temperature, or within a predetermined range of temperatures, for either of a predetermined period of time or continuously until otherwise altered by user intervention or by the occurrence of a predetermined event. For example, a predetermined range of temperatures in an exemplary, non-exclusive embodiment extends between approximately one hundred ten to one hundred twenty degrees Fahrenheit (~110-120° F.; ~43.3-48.9° C.), but in alternative embodiments can include any range of temperatures within the broader range of approximately one hundred five to one hundred thirty-five degrees Fahrenheit (~105-135° F.; ~40.5-57.2° C.)

Accordingly, in embodiments, the switchable control includes a timing apparatus suitable to set a target time or time period, or to monitor an elapsed time. A timing apparatus can include suitable timing circuitry and components (e.g., a crystal oscillator and corresponding circuitry), a mechanical timing device (e.g. clock with escapement, etc.), a solid-state timing device (e.g., integrated circuit), or any other suitable apparatus or combination of apparatuses. A timing apparatus may include a real-time clock and suitable features enabling either a user or a specially configured algorithm, to select a specific time at which to affect a change in the operational status of the heat generating device, such as by turning it on or off, altering a temperature thereof, reading an input from a thermal sensor, beginning or ending a predetermined operational mode or routine, reading a battery power level, or another action or combination of actions affecting the operation of the PTRD. Alternatively or additionally, a timing apparatus also typically includes features enabling either of the user or alternatively a specially configured algorithm, to select a duration (period) of time, which may be either variable or fixed, and may be either predetermined or determined in real time, against which a running of time will be measured.

Additionally, the switchable control 6 includes a tangible memory storage medium capable of storing coded instructions, including user-selected settings and preferences. In such embodiments, the memory storage medium will generally be operably coupled with data processing circuitry suitably configured to access the memory for storing information and for retrieving stored information, prior to, during, or following the execution of coded instructions. Such tangible memory storage medium can be removable or relatively permanently configured within the PTRD, or can be a part of an interoperable portable electronic device as shown in FIGS. 5 and 8 that is specifically configured with suitable coded instructions of a PTRD.

Because some portable electronic devices are configured with voice control technology, such as the SIRI technology of some portable devices available from Apple Inc. of Cupertino, Calif. (SIRI is a trademark of the Apple Inc.), at least one embodiment of the invention includes a switchable control including suitable hardware (e.g., a microphone, audio data processing circuitry, etc.) and machine-executable coded instructions to enable voice actuation of one or more of the user-selectable functions of the PTRD.

The head retention device 8 is configured to retain the heating element positioned in thermally conductive contact with a central portion of a user's forehead. At least a portion of the head retention device is generally configured to circumferentially embrace a portion of a user's head, in the manner, for example, of the headbands shown in FIG. 7. Additionally, the head retention device includes, in an embodiment, a brace portion 91 extending over at least a portion of the crown of the user's head, to limit an extent to which the heat generating device can displace downwardly relative to the user's head during use. Such brace portion can comprise one or more straps, an expanse or sheet of a flexible material (e.g., textile, polymer, etc.), or a rigid or semi-rigid structure curved to conform loosely or closely to the shape of a user's head, etc. The contemplated embodiments also encompass many other configurations of head retention devices, including but not limited to hats, helmets, hoods, scarves, and balaclavas, as shown in FIGS. 9a-9f.

In an exemplary embodiment, the head retention device is size adjustable, and includes a dimension-adjustment devices, materials or arrangements coupled with or within the head-embracing portion, enabling a user to obtain a tighter or looser fit about their head. Examples of such dimension-adjustment features in alternative embodiments include, but are not limited to, buckles, snaps, buttons, hook-and-loop fasteners, elastic elements, or any other size adjustment-enabling feature or material, or combination of features and materials, enabling a user to obtain a secure yet comfortable fit that retains the heating element in place during use.

In an embodiment, the head retention device includes a receptacle (e.g., pocket, fold, recess, etc.), fastener (e.g., clip, threaded fastener, pin, bracket, button, etc.) or other retaining device or arrangement (e.g. strap, magnet, hook-and-loop fastener, etc.), but can likewise include any other structure or material that is configured and suitable to securely couple the heating element with, and in position relative to, the head retention device. Such coupling can he either permanent or detachable, according to alternative embodiments.

Alternatively or additionally, either or both of an adhesive element and a friction-increasing feature, such as a pad, sleeve, layer, or other structure is disposed between a portion of the head-retaining device and either of the user's head or the heating element. The purpose of such adhesive and friction-increasing feature(s) is to assist in retaining the heating element in a result-affecting position centrally at the user's forehead. This can be aided by such features being disposed between the heating element and either of a portion of the head retention device or a portion of the user's head, or between a portion of the head retention device and a portion of the user's head, or any combination of such arrangements.

In a preferred embodiment, one or more layers of a sheet material, typically but not exclusively comprising a textile formed of either or both of natural and synthetic fibers, is interposed between the user-confronting surface 20 of the heating element and the user's forehead, For example, FIG. 6 depicts a heating element 2 disposed between plural sheet material layers 61/62 of a head band—e.g., in a pocket formed into the headband—wherein one of the plural material layers 62 is interposed between the heating element and the user's head during use. Preferably, such interposed material layer 62 readily permits heat transfer between the heating element and the user's head, while also helping to avoid burns, chafing, or other sources of discomfort that might result from direct contact between the heating element and the user's head. Such material layer will typically have a lower thermal conductivity than an equivalent thickness of a metal (e.g., copper, aluminum, steel, etc.), but a higher thermal conductivity than an equivalent thickness of a closed-cell material (e.g., neoprene, Styrofoam, etc.). and is considered 'substantially thermally-conductive' herein.

The power source 4 will most typically be configured for portability; either being worn or carried by the user. Therefore, as shown in the exemplary embodiment of FIG. 4, the power source typically includes one or more batteries 41, either disposable, or rechargeable and reusable. Examples of rechargeable batteries include lead-acid, nickel-cadmium, and nickel metal hydride type batteries, but are not limited to the examples listed here. Additionally, the batteries can be removable and replaceable, or can alternatively be generally sealed within a housing of the power source.

In rechargeable embodiments, the power source can be provided with a connection port (e.g., receptacle, etc.) to receive operable insertion of a connector of a recharging device, or can alternatively be provided with one or more prongs, whether fixed or foldable, configured to operably couple with an extrinsic power source or a recharging device. For example, the power source 4 can include a mini-USB (Universal Serial Bus) port 7 to receive insertion of a corresponding mini-USB connector of a recharging device. Alternatively, the power source 4 can include a two-prong plug configured for insertion into and electrical connection with a 110V AC outlet, and can further include circuitry for converting an input voltage into a form compatible with the batteries type of the power source.

In at least one embodiment, the power source can be a battery of a portable, powered device such as a music player, video player or another multimedia device, a camera, a portable phone, a portable computing device, an illumination device (e.g., a flashlight), or another device that derives its operating power from a battery. In such embodiments, a signal conveying means of the PTRD includes a connector configured at an end thereof to establish an electrically-conductive connection with a reciprocal connector or connection port of a portable, powered device, and to convey an operable electrical current between the portable powered device and the PTRD.

In at least one exemplary embodiment depicted in FIG. 5, a first portion of the connector of the PTRD signal conveying means is configured to couple (e.g., by insertion) with a port of a portable, powered device (e.g., a headphone port, or more typically, a port ordinarily utilized for recharging the portable, powered device), while another portion of the connector is configured to structurally and functionally replicate the port of the portable, powered device, and to operably receive connection of other devices that are configured to connect with the connection port of the portable, powered device. For example, the PTRD connector may be configured to couple with the headphone port of a music player, while also being configured to receive connection of a head phone 'plug.' Therefore, although being interposed between the headphone port and the headphone plug, the PTRD connector does not interfere with the function of either.

Different portable electronic devices can possess different types of power and signal ports, including relatively standardized formats such as mini-USB, and also a great multitude of proprietary connector configurations. Therefore, the contemplated embodiments also include providing an adapter device to increase user flexibility, and to expand the number of different portable electronic devices that can be used with a particular embodiment of the invented PTRD. For example, a first adapter device can be provided with a specially configured portion that plugs into a first portable electronic device.

The PTRD's signal conveying means can then be plugged into another portion of that adapter device to provide an operable interconnection. However, if the user then wants to use a second portable electronic device having a different port configuration, the user can select a second adapter device configured correspondingly to engage with the port of the second portable electronic device, and to likewise receive connection of the PTRD's signal conveying means.

A portion of the switchable control 6, in an embodiment, is disposed at an exterior surface of the PTRD and is manually-operable by a user. As shown in the alternative embodiments of FIGS. 1a and 1b, the manually-operable control can include a switch disposed at an exterior portion of either of the heating element or the power source, while being operably coupled with both.

Referring to FIG. 4, the switchable control typically includes a 'de-energize' setting and one or more 'energize,' or operational, mode settings. A user can select from among the one or more operational modes, such as the "Heat" and "Maintain" modes discussed supra. Additionally, a switchable control—which may include buttons, switches, dials, slides, or other actuators alternative to or in addition to those shown in FIG. 4, for example—can also be configured with multiple preset or user adjustable 'temperature settings,' 'time duration settings,' 'operation interval settings,' or 'thermostatic operation settings.'

Temperature settings ate used to establish an operating temperature of the heating element (e.g., a maximum temperature), or a maximum temperature to which a user's forehead will be heated (e.g., as sensed by a thermal sensor). A temperature setting will also generally be a temperature at which the heating element remains when operating in "Maintain" mode. A temperature setting can also be automatically determined by a preprogrammed algorithm that takes into account such factors as a user's identity (e.g., as indicated by user input), an ambient temperature, a temperature of a portion of the user's anatomy, as indicated in a signal received from an operably coupled thermal sensor), input from a power-management subroutine, etc. A temperature setting can be either a specified temperature or temperature range.

Time Duration settings are used to establish a duration of time during which the heating element will continue generating heat. When initially activating the PTRD, such time duration may also include a 'ramp up' time during which the heating element heats up from an ambient temperature to a predetermined or automatically determined temperature setting. Alternatively, a time duration setting can indicate either a duration of a period of time during which the heating element will maintain a particular temperature setting, or a duration of a period of time during which the heating element will remain inactive (e.g., not supplying heat), such as during an intermittent heating schedule as part of either a power-management subroutine or a predetermined operating mode.

Operation Interval (heating cycle) settings typically but not exclusively include alternating corresponding time duration and temperature settings. For example, an operation interval (or 'mode') setting can be termed "Active," for use when the user will be engaged in vigorous activities (e.g., skiing, hiking, etc.), and less heating is required from the PTRD. Therefore, setting operation interval can include either or both of coded instructions and circuitry configured to provide a moderate or low temperature setting, a moderate to low time duration for each interval of heating, and a large duration of time for each interval of inactivity between heating intervals. Conversely, an operation interval setting designated "Idle," for example, for use when the user will be involved in relatively passive activities (e.g., sitting and watching an outdoor event, etc.) can include a moderate to high temperature setting, a moderate to high time duration for each interval of heating, and a low duration of time for each interval of inactivity between heating intervals. Therefore, interval settings enable a user to select between plural operational modes, relative to the user's expected or actual needs for peripheral heating, and to control a highly tunable cycling of the heating function.

Alternatively, a power-management subroutine can include preprogrammed operation interval settings configured to extend the total operational duration of the PTRD before needing to recharge or replace a power source. A power-management subroutine can likewise be configured to dynamically alter one or more of the operation interval settings in response to a signal indicating either of a reduced or increased power condition of a power source.

In an advantageous embodiment, the switchable control includes coded instructions stored at a tangible data storage medium and executable by circuitry of as data processor, such as a processor of a portable electronic device. The coded instructions are configured, when executed by processing circuitry of the portable electronic device, to cause a visual display operably coupled with the data processor to display a graphical user interface (GUI) including, a user-selectable control icon. For example, the coded instructions can be provided in the form of a software application, or 'app' (herein, "PTRD app"), that can be accessed and downloaded to the portable electronic device from a remote source, or loaded to the portable electronic device from a portable data storage medium, or can be an application program preloaded onto the portable electronic device by a manufacturer or seller.

As shown according to the exemplary embodiment of FIG. 8, the coded instructions can be configured to present to a user any of numerous types of relevant information, including but not limited to:

a) ambient environmental conditions (e.g., temperature);
b) information indicating a user's physiological status (e.g., skin surface temperature, heart rate, etc.) as indicated by one or more sensors configured to detect such conditions and to produce a data signal indicative of the same;
c) operational data, such as a heating status, an elapsed time, a current temperature setting, a current heating element temperature, a current operation interval setting, a current power source level; a predicted remaining duration of available power, etc.; and
d) other data relevant to the operational status of a PTRD that may be useful to a user.

Additionally, control icons are displayed to a user in the exemplary embodiment depicted in FIG. 8. For example, the user can be presented with simple user-selectable control icons that allow the user to turn the PTRD on or off, and that enable the user to adjust the heat level up or down.

As previously mentioned, a GUI in an embodiment can likewise present to a user one or more control icons enabling the user to select from among plural optional temperature settings, time duration settings, operational interval settings, or power-management settings. The coded instructions corresponding to each such control icon are operably coupled, in response to a selection of the control icon by a user, to call upon one or more corresponding subroutines of coded instructions configured, when executed by the processing circuitry, to cause an indicated response by one or both of the heating element and the power supply.

Alternatively, selection of a control icon corresponding to a particular operational, mode may not immediately affect a response in the heating element, but instead causes a programmed subroutine to begin monitoring for the occurrence of it predetermined or user-selected condition that will, in turn, responsively elect either or both of the heating element and the power source. For example, an operational mode may be configured to actuate the heating element upon detection, by an operably coupled sensor, that the ambient environmental temperature has reached thirty-two degrees Fahrenheit (32° F.; or 0° C.) or below. In such example, detection that the ambient atmospheric temperature corresponds to a predetermined value is a predetermined condition, the occurrence of which prompts the switchable control to responsively activates the heating element.

The invented PTRD embodiments additionally benefits from inclusion of one or more peripheral thermal sensor or other sensor devices configured to sense a thermal condition of a user's extremities, such as a dermal temperature condition, to beneficially affect operation of the PTRD. For example, with reference to FIG. 7, a thermal sensor 71 configured to detect a dermal thermal condition of the user can be disposed at and coupled in close proximity to the skin of a user's hand, foot, or another anatomical extremity located remotely from the heat generating device 2. Such coupling be accomplished through the use of a retaining device 72 (e.g., an elastic band or cuff 73, a finger-worn ring, etc.), an adhesive, or an item of the user's clothing (e.g., a glove, wristband, garment cuff or sleeve, etc.) configured to retain the thermal sensor device 71 in position.

Although a typical embodiment of a peripheral thermal sensor directly indicates a thermal condition of a user's extremity, such as by measuring a skin surface temperature, the embodiments are not so limited. Alternatively, or additionally, a provided peripheral sensor can detect a skin color (or a change in color relative to a baseline skin color), a change of blood flow, or even a change in the circumference in an peripheral appendage (e.g., a finger diameter, etc.), and will nonetheless be considered a 'peripheral thermal sensor' herein. For example, it is well-known that a ring is easier to remove when a finger is cool than when it is warm, due to decreased blood flow and a resulting decrease in circumference of the finger in cooler temperatures.

A peripheral thermal sensor 71 in the contemplated embodiments is configured to convey to the switchable control information indicative of a user's peripheral thermal condition. For example, in an exemplary embodiment, the thermal sensor device includes circuitry and a transmitter configured to transmit a wireless signal 74 including information indicative of the user's detected dermal thermal condition. The switchable control correspondingly includes a receiver configured to receive such wireless signal transmitted from the sensor, and to convey a signal including the transmitted dermal thermal condition information to the processing circuitry of the switchable control. The data processor, in turn, includes interoperable coded instructions and data processing circuitry suitable to interpret the information indicative of the user's dermal thermal condition, and to affect an actuation condition of the heat generating device in response to such information.

The contemplated embodiments include any wireless signaling technology suitable to transmit information-bearing signals over short distances as described. In particular, an exemplary embodiment utilizes so-called Bluetooth technology, and suitably configured transmitters and receivers, to enable conveyance of signals between the described components of a PTRD.

Alternatively, a conductive lead 75 (e.g., a wire, cord, cable, etc.) extends from the thermal sensor to a switchable control 76 and is operably coupled with each. In at least one embodiment, either or both of the thermal sensor 71 and a conductive lead 75 are integrated into a user's garment(s), obviating a need for the user to separately don each of the several components. Instead, simply donning a jacket, for example, places one or more integrated thermal sensors in position to detect and convey to the switchable control a thermal condition of one or more of the user's peripheral anatomical regions.

As previously noted and mentioned here again, the switchable control can be either integrated with one or both of the heating element and the power source, or can be a separate but operably coupled component. For example, the switchable control can be retained in a pocket formed into the user's garment (e.g., jacket, sweater, shirt, pants, etc.). Therefore, for embodiments wherein the power source and the switchable control are integrated into a unitary device, the switchable control can be detached from the heating element during charging and recharging of the power source, for example.

In at least one embodiment, any one or more of the heating element, switchable control, and one or more peripheral thermal sensors, utilizes a power source that is independent from the power source used by at least one other of such components. For example, when physically separated from the switchable control as in one of the described wireless signaling embodiments, a peripheral thermal sensor may include or otherwise be operably coupled with a power source that is independent from the power source for the heating element. Such arrangement provides a user with substantial flexibility in positioning the sensor proximate to a selected body part.

In an embodiment, the power source 4 either includes or is operably coupled with photovoltaic elements configured to produce power when exposed to light. Such photovoltaic elements can be disposed at a surface of one or more of the switchable control or the heating element, or can alternatively or additionally be coupled with or integrated into a portion of a user's garment Where sufficient light exposure is available, and where the photovoltaic elements are sufficient in number, size, efficiency, and output, the power derived from the photovoltaic elements can be utilized to operate one or more of the heating element, the switchable control, and one or more thermal sensors. Alternatively or additionally, such light-derived power can be used to recharge batteries of the power source either concurrently with operation of the PTRD, or when one or more of the heating element and the switchable control is de-energized or otherwise placed in an inactive or resting condition.

Further, according to a particularly beneficial embodiment, the processing circuitry and coded instructions of the PTRD are configured to cause the PTRD to responsively switch between, or to concurrently utilize, power derived from both batteries and photovoltaic elements. By doing so, the PTRD can be continuously utilized for a significantly longer duration than is possible by utilizing either power source individually.

Figure 10:
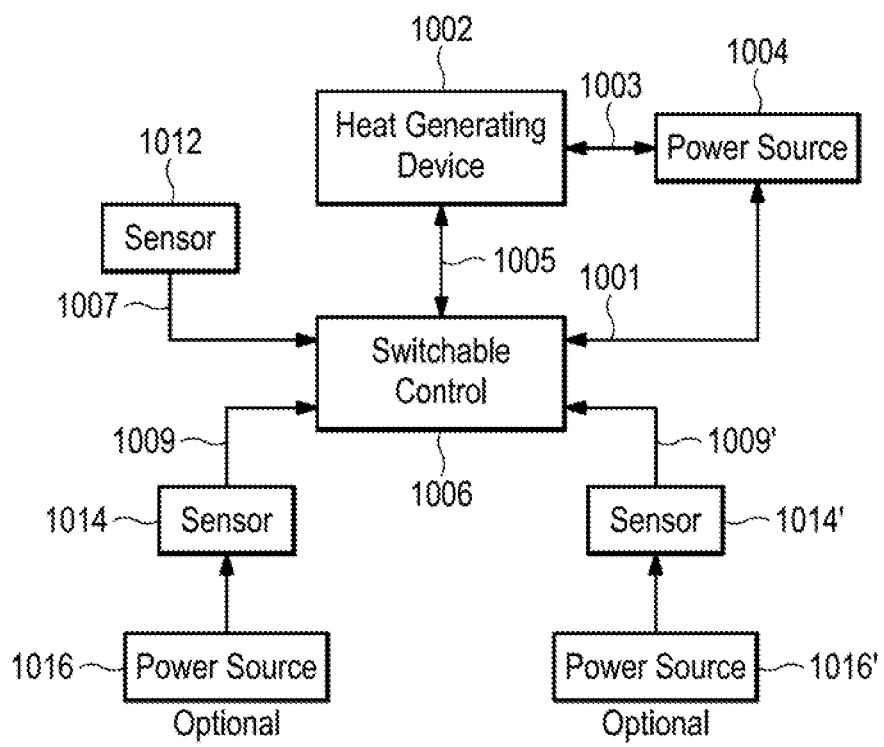
FIG. 10 depicts a block diagram of a PTRD including optional peripheral sensors and power sources, according to an embodiment of the invention.

FIG. 10 depicts an exemplary set of signal pathways between the several components of a PTRD according to an embodiment. However, not all of the depicted signal pathways are necessarily present or identically configured in all embodiments.

As shown at 1001, signals are typically conveyed hi-directionally between the switchable control 1006 and the power source 1004. In one instance, the signal pathway 1001 conveys an operating electrical current from the power source to the switchable control to energize the switchable control, and can likewise include a return pathway configured as a ground. A signal pathway 1003 likewise generally exists between the heat generating device 1002 and the power source 1004, to convey an energizing electrical current to the heat generating device. Such signal pathways may typically be embodied as a conductive lead, such as a metal wire or a conductive trace on a printed circuit board. In another instance, the signal pathway 1001 conveys to the switchable control a signal indicative of a power level status of the power source.

In a typical embodiment, in addition to signal pathways 1001 and 1003, a third electrical signal pathway 1005 is provided between the switchable control and the heat generating device. During operation, actuating a control of the switchable control closes an electrical circuit that includes each of the power source, the heat generating device and the switchable control, enabling the heat generating device to produce heat. The switch can be manually operable, or may be automatically operable by a command produced by data processing circuitry executing coded instructions. As would be understood by an ordinarily skilled artisan, such switch can be either of a mechanical switch, a solid state switch circuit, or a combination thereof. Conversely, de-activating a switch of the switchable control, and thus opening the circuit, causes an electrical current to cease flowing along pathways 1001, 1003 and 1005, and the heat generating device ceases producing heat. As shown in FIG. 10, the electrical circuit can be configured to convey an electrical current in either direction, from the power source to the heat generating device to the switchable control, or instead in the reverse direction.

Additionally, when provided in an embodiment, a signal indicative of a thermal condition is conveyed along signal pathway 1007 to the switchable control from a thermal sensor of a head retention feature. Likewise, signals from one or more peripheral thermal sensors 1014 or 1014', when present in an alternative embodiment, are conveyed along signal pathways 1009 and 1009', respectively, to the switchable control 1006. One or more of signal pathways 1007, 1009 and 1009' can be either wired or wireless (e.g., using Bluetooth technology), as described above.

Each of sensors 1012, 1014 and 1014' can derive operational power directly from power source 1004; however, in a more typical embodiment, the sensors will derive power conveyed from the power source through the switchable control, or may even derive power from a local power source such as 1016/1016' either located on board each sensor, co-located with each sensor, or otherwise located separately from the main power PTRD supply 1004 but coupled in communication with each of a sensor and the switchable control.

FIGS. 11-14 depict several operational logic flows, according to alternative exemplary embodiments of the invention. Such logic flows may be embodied in any of numerous software application programming architectures. Most notably in exemplary embodiments, the processes and operations depicted in the illustrated logic flows are embodied in commonly available application software and architectures, for example, from the Apple Inc. developer web site (http://developer.apple.com), or from the Google Inc. developer web site (http://developer.android.com), although these well-known examples do not limit the scope of the contemplated embodiments.

Figure 11:
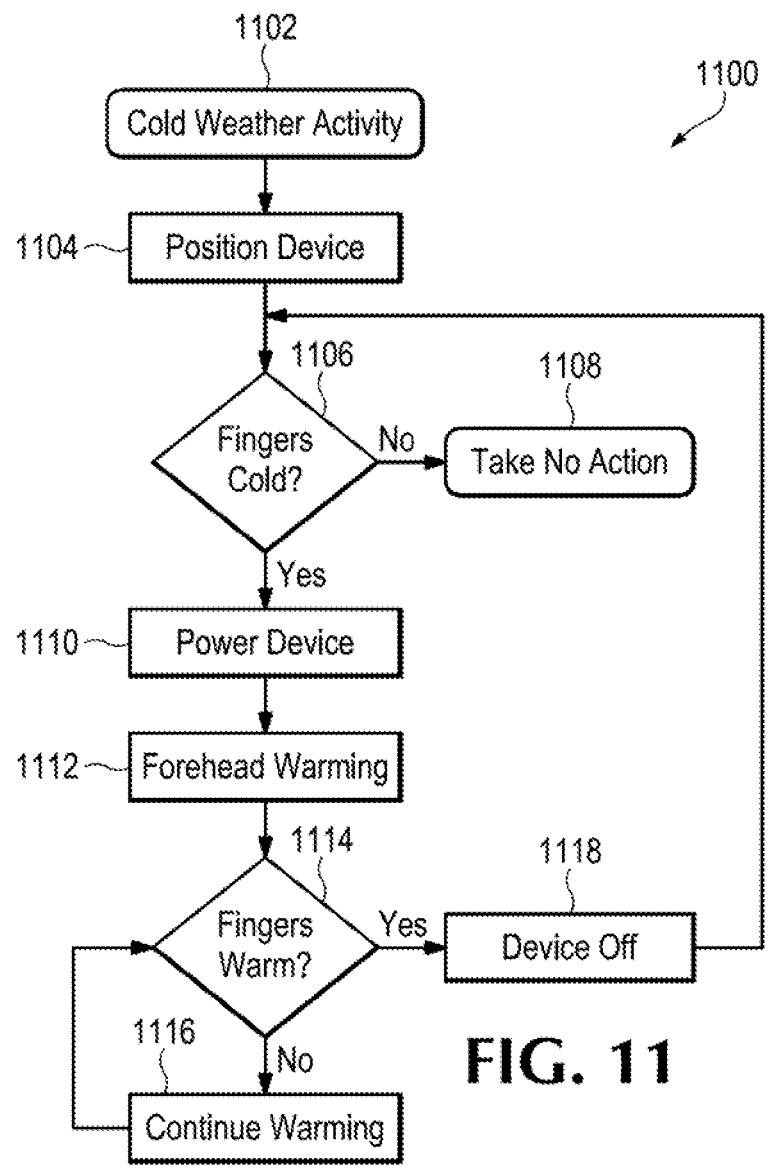
FIG. 11 depicts an general operational logic flow diagram of a PTRD having a dual mode of operation, according to an embodiment of the invention.

FIG. 11 depicts a basic operational logic flow 1100 of a PTRD. When a user either encounters or contemplates encountering a cold environment or a cold weather activity, at 1102, the user will position the PTRD for use as described above, including each of the heating element, the head retention device, etc. At any time while exposed to or even prior to entering the cold environment, the user assesses, at 1106, whether his fingers or other portions of his extremities feel cold. If not, the user generally need not take any action 1108.

However, if the user's fingers are cold, the user will engage power to the device via the switchable control, as at 1110, supplying an electrical current from the power supply to the heating element.

Generally, as long as the electrical current is maintained, forehead warming 1112 by the heating element continues. However, at any time, the user can assess, at 1114, whether his fingers feel warm. If not, then the user takes no action, and forehead warming continues 1116, with self-assessment repeating periodically. However, if the user's fingers feel warm, user can turn off the device, 1118, via the switchable control. As shown in FIG. 11, the logic flow then returns again to the user's periodic self-assessment (or sudden realization) of the thermal condition of his extremities.

Figure 12:
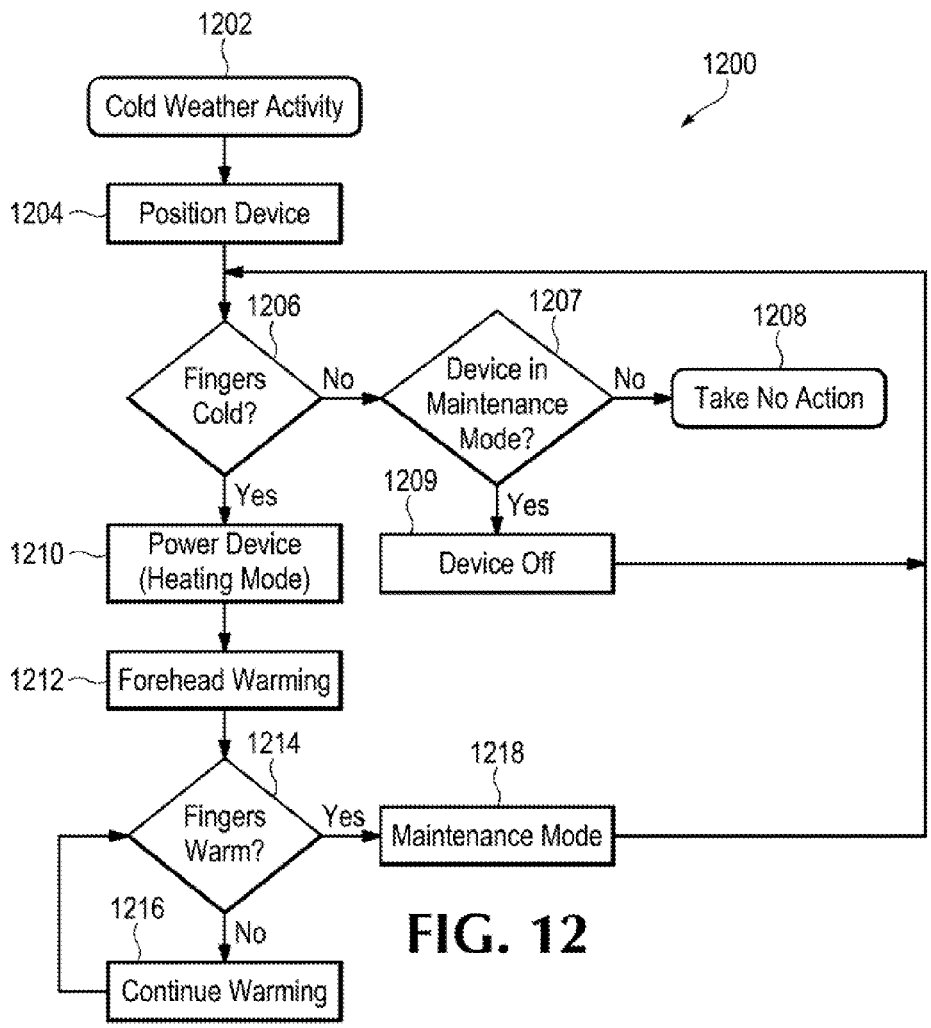
FIG. 12 depicts an general operational logic flow diagram of a PTRD including one or more peripheral sensors, according to an embodiment of the invention.

FIG. 12 depicts a very similar logic flow 1200 for a dual mode PTRD (having a maintenance mode setting), with several of the operations (e.g., 1202, 1204, 1206, 1210, 1212, 1214, and 1216) remaining basically the same as their counterparts in the example of FIG. 11. Different actions may result, however, following each of the decision points 1206 and 1214.

At 1214, for example, if the user determines that his fingers are warm, rather than turning off the device (although that remains an option exercisable at 1218), the user can instead place the device into maintenance mode, at 1218, generally via the switchable control.

Further, if the user determines at 1206 that his fingers are not cold, the user next determines at 1207 whether the PTRD is presently operating in maintenance mode. If the PTRD is operating in maintenance mode, the user can then choose to turn off the PTRD, at 1209, and the logic flow then returns again to the user's periodic self-assessment (or sudden realization) of the thermal condition of his extremities. Of course, the user can also choose to leave the device in maintenance mode, in which case the operational logic flow remains the same as if the user had just activated maintenance mode at 1218.

Figure 13:
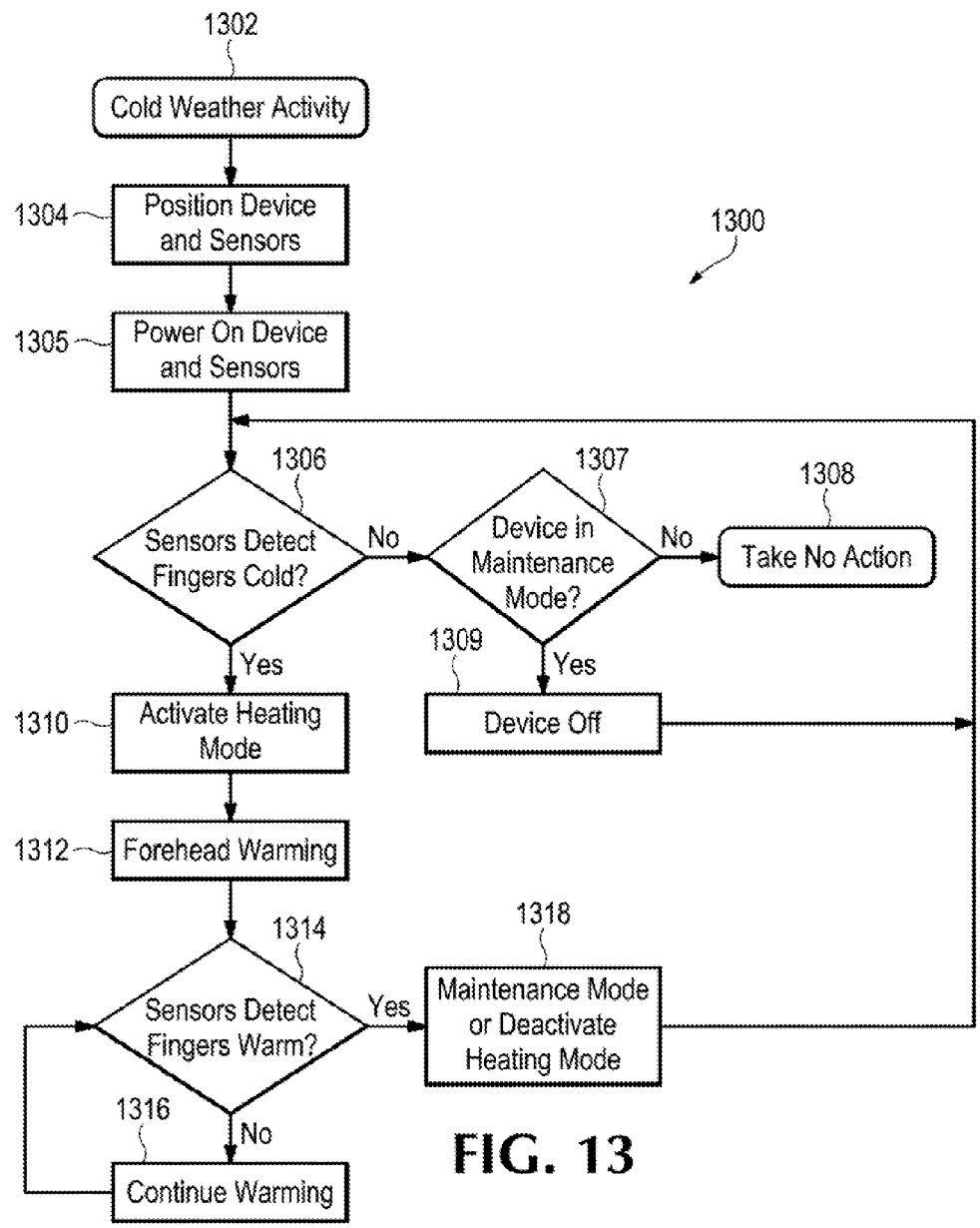
FIG. 13 depicts an general operational logic flow diagram of a PTRD including a PTRD software application operating on a portable electronic device, according to an embodiment of the invention.

FIG. 13 depicts an operational logic flow for a PTRD embodiment that includes peripheral sensors. When a user either encounters or contemplates encountering a cold environment or a cold weather activity, at 1302, the user will position both the PTRD and one or more peripheral sensors for use, at 1304, as described above.

Unlike in the operational flows of FIGS. 11 and 12, however, the PTRD device and sensors are powered on at 1305 in the exemplary embodiment depicted in FIG. 13. In particular, the sensors are placed into an active, sensing condition, so that at 1306, the sensors, rather than (or in addition to) the user himself, can detect whether or not his fingers or other sensor-monitored extremities are cold. If they are not cold, then no action needs to be taken, as at 1308. However, if they are cold, then either the PTRD can notify the user via some user-detectable indication (e.g., audible, sensory, etc.) and the user activates a heating mode at 1310 via the switchable control, or data processing circuitry associated with the PTRD can execute coded instructions configured to activate the heating mode at 1310 in response to a signal from one or more of the thermal sensors.

At 1312, warming of the forehead continues following activation of the heating mode, while the one or more peripheral sensors either continuously or periodically monitor a thermal condition of the user's fingers or other extremities at 1314. As described above relative to FIGS. 11 and 12, if the fingers are determined to not yet be warm, at 1314, then warming will continue at 1316.

If the signal from a sensor indicates that the fingers are warm, however, which is to say that a sensed thermal condition meets or exceeds a predetermined (e.g., factory set or user selected) threshold temperature, then at 1318, the PTRD can either default into a maintenance mode, or alternatively, the heating mode can be deactivated. Either or both of these options can be controlled by data processing circuitry executing coded instructions, or they can be user selected via the switchable control.

FIG. 4 depicts an operational logic flow according to still another embodiment of the invention, which includes not only peripheral sensors, but also a switchable control embodied as a PTRD app operating on a portable electronic device, such as a smart phone, a portable multimedia device (e.g., music player, digital camera, etc.).

Through the powering on of the device and sensors, at 1404, the operational actions correspond closely with those at 1302-1305 in FIG. 13. However, at 1405, the user additionally activates the PTRD app on the portable electronic device. In at least one embodiment, activating the PTRD app also powers on the PTRD device and sensors, or vice versa, such that the operations at 1404 and 1405 occur either concurrently or sequentially.

As with many well-known applications operating on a mobile device for other purposes, a PTRD app can be activated by touching an icon presented at a touch screen, or by selecting the application from a menu, or the PTRD app may be set to automatically actuate when the portable electronic device is turned on. Alternatively, some portable devices can be configured with a thermal sensor to determine to temperature of an ambient environment, and can be set to automatically activate the PTRD app when the thermal sensor of the portable device detects that an ambient temperature is at or below a predetermined threshold temperature.

As in the embodiment of FIG. 13, if the sensors do not detect that the fingers or other monitored extremities are cold, at 1406, then no action is taken 1408. However, if the sensors detect a cold thermal condition of the fingers or other extremities, then the heating element, is activated 1410, and forehead warming begins 1412. The remainder of the operations at 1414-1418 in FIG. 14 correspond with those at 1314-1318 of FIG. 13.

Figure 14:
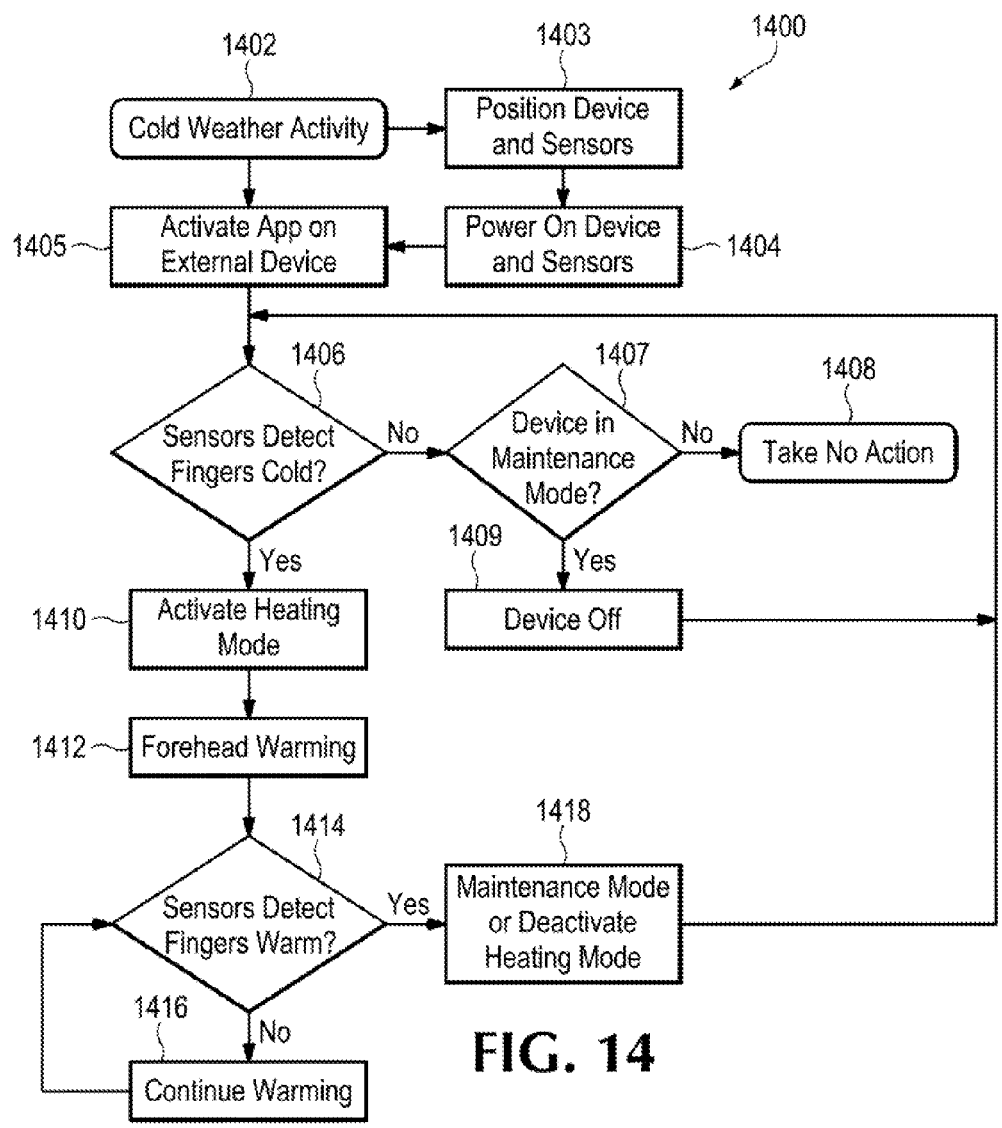
FIG. 14 depicts an general operational logic flow diagram of a PTRD, according to an embodiment of the invention.

At any point during the operations shown according to the embodiment in FIG. 14, or any of a number of other contemplated PTRD app-enabled embodiments, the user can monitor or affect one or more operational activities, settings, modes, conditions or other functions of the PTRD via a user interface of the portable electronic, including a GUI in one or more embodiments, as described above relative to FIG. 8. Further, according to an embodiment, a user can establish one or more user profiles, including one or more user-selected operational parameters, or preferences, according to which the user can cause the PTRD to operate during any particular use session.

Likewise, different user profiles can be established of one or more other users, or alternative profiles for a particular user. Such profiles can be stored at a tangible data storage medium coupled with the PTRD, or integrated into the PTRD, or loadable into and readable by the PTRD, or receivable by a receiver of the PTRD as data transmitted wirelessly (via e.g., BlueTooth technology, Wi-Fi technology, cellular phone signal, etc.) from another device (e.g., another portable electronic device, a home computer, a remote server device, etc.). Each profile can be separately identified by a unique identifier (e.g., a user-designated title), and can be implemented by selecting such identifier from a menu of available profile identifiers for execution by the PTRD. Such options are particularly suited to including in a PTRD app, and profiles can be shared between users via commonly known methods for sharing apps between portable electronic devices.

Although FIGS. 11-14 demonstrate several operational logic flows according to alternative embodiments, an ordinarily skilled artisan will likewise recognize that a PTRD can likewise take a form not specifically addressed in those drawing figures, and will remain within the scope of the contemplated embodiments. For example, a contemplated embodiment includes a PTRD app even without peripheral sensors. Likewise, a dual warming mode can be also included in embodiments with peripheral sensors, or with a PTRD app, or with both. Therefore, an ordinarily skilled artisan will recognize that FIGS. 11-14 are illustrative of exemplary embodiments, but that the invented and contemplated embodiments are not limited to those drawing figures.

It will be understood that the present invention is not limited to the method or detail of construction, fabrication, material, application or use described and illustrated herein. Indeed, any suitable variation of fabrication, use, or application is contemplated as an alternative embodiment, and thus is within the spirit and scope, of the invention.

It is further intended that any other embodiments of the present invention that result from any changes in application or method of use or operation, configuration, method of manufacture, shape, size, or material, which are not specified within the detailed written description or illustrations contained herein yet would be understood by one skilled in the art, are within the scope of the present invention.

Finally, those of skill in the art will appreciate that the invented method, system and apparatus described and illustrated herein may be implemented in software, firmware or hardware, or any suitable combination thereof. Preferably, the method system and apparatus are implemented in a combination of the three, for purposes of low cost and flexibility. Thus, those of skill in the art will appreciate that embodiments of the methods and system of the invention may be implemented by a computer or microprocessor process in which instructions are executed, the instructions being stored for execution on a computer-readable medium and being executed by any suitable instruction processor.

Accordingly, while the present invention has been shown and described with reference to the foregoing embodiments of the invented apparatus, it will be apparent to those skilled in the art that other changes in form and detail may be made therein without departing from the spirit and scope of the invention as defined in the appended claims.

We claim:

1. A personal thermal regulating device (PTRD), comprising:
   a heat-generating device;
   a power source;
   a switchable control operably coupled with each of the heat generating device and the power source;
   a head retention device configured to retain the heat generating device positioned centrally at and in thermally conductive contact with a user's forehead during use; and
   a remote thermal sensor device coupled with a retention means configured to retain the thermal sensor device in close proximity to the user's skin at a portion of a user's anatomical extremities, the thermal sensor device suitably configured to detect a dermal thermal condition of the user and to produce a signal indicative of the detected dermal thermal condition.

2. The PTRD of claim 1, wherein a user-confronting surface of the heat generating device includes a left-to-right concave curvature configured to correspond to a curvature of a user's forehead during use.

3. The PTRD of claim 1, further comprising a thermal sensor coupled with the heat generating device and configured to detect a thermal condition of either or both of a portion of the heat generating device and a portion of the user's forehead.

4. The PTRD of claim 1, wherein the switchable control is disposed at an exterior surface of the PTRD and is manually-operable by a user.

5. The PTRD of claim 1, wherein the switchable control includes coded instructions configured, when executed by processing circuitry of a portable electronic device, to cause a visual display portion of the portable electronic device to display a graphical user interface (GUI) including a user-selectable control icon.

6. The PTRD of claim 1, wherein the power source includes a battery.

7. The PTRD of claim 6, wherein the battery is rechargeable.

8. The PTRD of claim 6, wherein the battery is removable and replaceable.

9. The PTRD of claim 6, wherein the battery is housed within a portable electronic multimedia device.

10. The PTRD of claim 1, wherein the heat generating device and the power source are configured for coupling at separate portions of a head retention device.

11. The PTRD of claim 1, wherein the switchable control includes a de-energize setting and plural energize mode settings.

12. The PTRD of claim 1, wherein the head retention device is configured to circumferentially embrace a portion of a user's head and includes one or more of a dimension-adjustment device, material and arrangement, enabling the user to obtain a tighter or looser fit about their head.

13. The PTRD of claim 1, wherein the head retention device includes an elastic band configured to compressively retain the head retention device in position relative to a user's head during use.

14. The PTRD of claim 1, wherein the head retention device includes a pocket formed between plural material layers, the pocket being suitably dimensioned to receive and retain either or both of the heat generating device and the switchable control.

15. The PTRD of claim 1, wherein the head retention device is selected from the group consisting of a strap, a hat, a hood, a helmet, a balaclava, and a scarf.

16. The PTRD of claim 14, wherein a first material layer of the plural material layers is configured to interpose between the head generating device and the user's forehead during use, and where the first material layer is substantially thermally-conductive.

17. The PTRD of claim 10, wherein an electrically conductive lead is configured at a first end thereof to operably couple with a connection port of an electrically-powered portable electronic device and to receive conduction of an operable electrical current therefrom.

18. The PTRD of claim 17, wherein a portion of the first end is further configured to replicate the connection port of the portable electronic device, and another portion of the first end is configured to operably receive connection of devices that are configured to connect with the connection port of the portable electronic device.

19. The PTRD of claim 1, the retention means is a portion of a user-wearable garment item.

20. The PTRD of claim 1, wherein the signal indicative of the user's detected dermal thermal condition is a wireless signal.

21. The PTRD of claim 1, wherein the switchable control further comprises:
   a receiver configured to receive the signal produced by the remote thermal sensor; and
   a data processor configured with interoperable coded instructions and data processing circuitry suitable to interpret information in the signal, and to affect an actuation condition of the heat generating device in response to such information.

22. The PTRD of claim 1, wherein the switchable control further comprises:
   a transmitter configured to transmit a wireless control signal to the heat generating device.

23. The PTRD of claim 22, wherein the transmitter is configured to transmit the wireless control signal via Bluetooth signal technology.

24. The PTRD of claim 1, wherein the switchable control includes heat cycle controls operably coupled with the heat generating device and comprising either or both of circuitry and device-executable instructions configured, when executed by a data processor of the switchable control, to affect one or more of a duration of a heat generating instance, a duration of a delay between heat generating instances, and a heat generating cycle frequency.

25. The PTRD of claim 24, wherein the heat cycle controls are manually operable.

26. The PTRD of claim 24, wherein the switchable control further comprises battery charge level detection circuitry.

27. The PTRD of claim 26, wherein the switchable control is configured, upon detecting a low charge level condition of the power source, to execute the heat cycle controls in a manner pre-determined to extend an operable duration of the power source.

28. The PTRD of claim 19, wherein the user-wearable garment item is selected from the group consisting of a glove, a mitten, a ring, a wristband, an ankle band, as sleeved shirt, a pant, a shoe, and a sock.

29. The PTRD of claim 1, wherein the head retention device includes a brace portion extending over as crown of the user's head, and configured to limit an extent to which the heat generating device can displace downwardly relative to the user's head during use.

* * * * *

UNITED STATES PATENT AND TRADEMARK OFFICE
CERTIFICATE OF CORRECTION

PATENT NO. : 8,907,251 B2
APPLICATION NO. : 14/169110
DATED : December 9, 2014
INVENTOR(S) : Walter G. Larsen and Michael J. Adler It is certified that error appears in the above-identified patent and that said Letters Patent is hereby corrected as shown below:

In the Claims

Column 18:
at line 16, replace "a mitten, a ring, a wristband, an ankle band, as sleeved shirt," with --a mitten, a ring, a wristband, an ankle band, a sleeved shirt,--

Column 18:
at line 19, replace "device includes a brace portion extending over as crown of the" with --device includes a brace portion extending over a crown of the--

Signed and Sealed this
Thirty-first Day of March, 2015

Michelle K. Lee
*Director of the United States Patent and Trademark Office*